(12) United States Patent
La Loggia et al.

(10) Patent No.: US 6,169,178 B1
(45) Date of Patent: Jan. 2, 2001

(54) PROCESS FOR THE PREPARATION OF 16,17 ACETALS OF PREGNANE DERIVATIVES WITH CONTROL OF THE EPIMERIC DISTRIBUTION AT THE C-22 POSITION

(75) Inventors: Filippo La Loggia, Gropello Cairou; Paolo Petacchi, Paullo, both of (IT)

(73) Assignee: Farmabios S.r.l. (IT)

( * ) Notice: Under 35 U.S.C. 154(b), the term of this patent shall be extended for 0 days.

(21) Appl. No.: 09/067,711

(22) Filed: Apr. 28, 1998

(30) Foreign Application Priority Data

Apr. 30, 1997 (IT) .............................................. MI97A0111

(51) Int. Cl.$^7$ ..................................................... C07J 71/00
(52) U.S. Cl. ................................................................. 540/63
(58) Field of Search .................................................. 540/63

(56) References Cited

U.S. PATENT DOCUMENTS

| | | |
|---|---|---|
| 2,998,433 | 8/1961 | Schaub et al. . |
| 3,047,468 | 7/1962 | Origoni et al. . |
| 3,549,498 | * 12/1970 | Diassi et al. ............................ 195/51 |
| 3,928,326 | 12/1975 | Brattsand et al. . |
| 4,432,976 | * 2/1984 | Annen et al. .......................... 424/241 |
| 4,695,625 | * 9/1987 | Macdonald ............................. 540/63 |
| 5,451,690 | * 9/1995 | Devocelle et al. .................... 552/566 |

FOREIGN PATENT DOCUMENTS

| | | |
|---|---|---|
| 0164636A | 12/1985 | (EP) . |
| 0262108 | 3/1988 | (EP) . |
| 0508900 | 10/1992 | (EP) . |
| 0262108A | 3/1998 | (EP) . |
| 1429922 | 3/1976 | (GB) . |
| 1469575A | 4/1977 | (GB) . |
| 9213872A | 8/1982 | (WO) . |
| 9104984 | 4/1991 | (WO) . |
| 9211280A | 7/1992 | (WO) . |

* cited by examiner

*Primary Examiner*—Barbara Badio
(74) *Attorney, Agent, or Firm*—Hedman, Gibson & Costigan, P.C.

(57) ABSTRACT

Described herein is a process for the preparation of an acetal of formula (I) in which $R_1$ is an alkyl, $R_2$ is H or an acyl, X is β-OH and Y is H, comprising the acetalization with control of the epimeric distribution at the C-22 position, for treatment with $R_1$ CHO in aqueous HBr or HI of a compound of formula (II) in which $R_2$ has the meaning specified above, $R_3$ and $R_4$ are both H, or, taken together, are —$C(R_5)(R_6)$—, where $R_5$ and $R_6$, which may be the same or different from one another, are alkyl groups, and X and Y are chosen from among the following:

A) X and Y, taken together, are an additional bond between C-9 and C-11;
B) X is β-OH, and Y is H or an α-halogen;
C) X is β-$OR_7$ where $R_7$ is an acyl, and Y is H or an α-halogen; and
D) X and Y, taken together, are —O—.

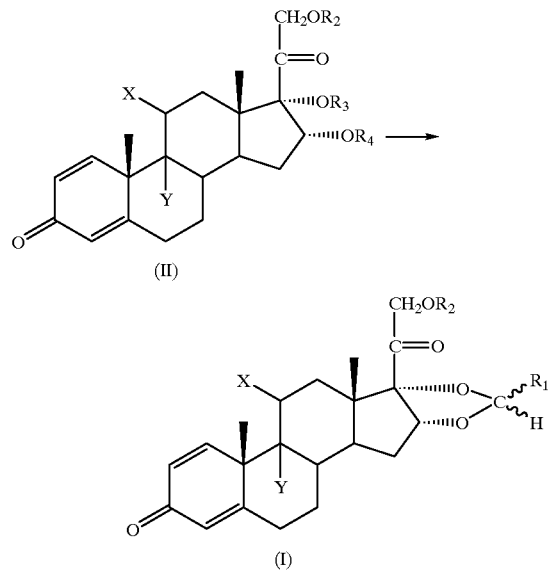

31 Claims, No Drawings

US 6,169,178 B1

PROCESS FOR THE PREPARATION OF 16,17 ACETALS OF PREGNANE DERIVATIVES WITH CONTROL OF THE EPIMERIC DISTRIBUTION AT THE C-22 POSITION

FIELD OF INVENTION

The present invention regards a new process for the preparation of 16,17 acetals of pregnane derivatives, in particular of budesonide [16,17-butylidenebis(oxy)-11,21-dihydroxy-pregna-1,4-diene-3,20-dione], a glucocorticoid having an anti-inflammatory activity.

Budesonide and other structurally correlated glucocorticoids were described for the first time in the patent application GB 1.429.922 and in the patents of the same family in the name of Bofors. Owing to the presence of the acetal carbon atom C-22, budesonide and its structural analogues exist in the form of epimers at the C-22 position. The epimer C-22 R, sometimes also referred to as epimer B, is for budesonide, and more in general for its structural analogues, the more active from a pharmacological standpoint.

The present invention regards, in particular, a process for the preparation of budesonide and of 16,17 acetals of pregnane derivatives structurally correlated thereto, comprising treating with aldehydes 16,17-diols, or of 16,17-ketals or cyclic acetals, in the presence of aqueous hydrobromic acid or hydriodic acid, used as reaction catalysts and solvents.

Unexpectedly, when operating in aqueous HBr or HI, it is possible to control as desired the epimeric ratio at the C-22 position, obtaining high yields both of R epimer-enriched mixtures and of mixtures containing the epimers R and S in approximately equal amounts.

TECHNICAL PROBLEM

From the standpoint of the pharmacological activity, it is undoubtedly important to have available processes for the preparation of budesonide and of the glucocorticoids with anti-inflammatory activity structurally correlated thereto, that prevalently lead to the production of the R epimer, which is pharmacologically the more active.

However, from a practical point of view, it is useful to have available processes of synthesis that allow to control the epimeric ratio as desired, so as to be able synthesize, even mixtures with R/S epimeric ratios of between 60/40 and 50/50 in high yields and using industrial methods. In the case of budesonide, in fact, these mixtures are of considerable interest from the commercial standpoint, in so far as they are the ones for which, in various countries, health registration has been obtained and is still valid.

PRIOR ART

The patent application GB 1,429,922 describes the synthesis of budesonide and its structural analogues by treatment of the corresponding 16α,17α diols of 11β,21-dihydroxy-pregna-1,4-diene-3,20-diones with aldehydes, in dioxane, in the presence of perchloric acid. This method yields mixtures of epimers at the C-22 position, the separation of which is difficult and may be obtained only using far from practical techniques from the industrial standpoint, such as the molecular-exclusion chromatography described in U.S. Pat. No. 3,928,326.

The ketalization in dioxane and perchloric acid does not allow the ratio between the R and S epimers to be controlled, this ratio varying very little even if the reaction temperature is changed, and moreover depending upon the substrate used. In fact, as illustrated by the comparative data of the applicant given later in the present text, in order to obtain mixtures of 22R and 22S epimers in approximately equal quantities, it is necessary the presence on the pregnane nucleus of a free hydroxyl group both in the position 11β and in the position 21. In the absence of just one of these free hydroxyl groups, mixtures of epimeric acetals are obtained in which the diastereoisomer S, which is less active pharmacologically, prevails.

WO 91/04984 describes the preparation of budesonide as a mixture of 22R epimers: 22S epimers in the ratio of approximately 1:1 by treatment of 16-α-hydroxy-prednisolone with butyraldehyde, in acetonitrile, in the presence of para-toluenesulphonic acid.

EP-A-164636 describes the preparation of budesonide and of structurally correlated 16,17 pregnane acetals in the form of mixtures in which the R epimer prevails, by transketalization with butyraldehyde in aqueous HF of the corresponding 16-α,17-α acetonides (or 16,17-diols) of 16-α-hydroxyprednisolone.

The use of HF, which is notably corrosive, presents the drawback of requiring special equipment, with the consequent increase in industrial costs of production, and moreover is not suitable for obtaining mixtures of 22R and 22S epimers in approximately equal quantities, in so far as it does not enable to obtain at the same time the complete conversion into the desired acetals, stopping at the desired R/S epimeric ratio. In fact, as shown by Examples 1 and 3 of EP-A-164.636, when operating in aqueous HF, it is possible to obtain the 22R and 22S epimers in approximately equal quantities only at extremely low temperatures (of about −78° C.), which it is practically impossible to be obtained in industrial systems. Furthermore, at such temperatures, even after prolonged reaction times, high quantities (approximately 40%) of non-reacted starting product are found. The conversion of unreacted 16,17-acetonide in the desired acetal calls for the use of higher temperatures (approximately of from −10° C. to 0° C.), at which temperatures, however, mixtures are isolated that are markedly enriched in R epimer (approximately 90%), without it being possible to obtain 22R/22S mixtures in ratios of from 60/40 to 50/50. Similar problems are encountered when operating in aqueous HCl, where in addition the reaction product is obtained in a less pure form.

EP-A-262,108 describes a method for controlling the epimeric distribution of 11β-OH 16,17-acetals of pregnane derivatives by reacting the corresponding 16,17-diols or 16,17-acetonides with carbonyl compounds in the presence of acid catalysts, preferably perchloric acid, in hydrocarbon or halogenated hydrocarbon solvent, such as chloroform or methylene chloride (somewhat toxic solvents, the use of which is preferably to be avoided or at least limited), possibly in the presence of dimethyl formamide or dimethyl sulphoxide as regulators of the epimeric distribution (these latter solvents are difficult to be removed from the end product owing to their high boiling point).

EP-A-262,108 moreover describes a method for obtaining prevalently the 22R epimer by treatment of 16,17-diols or acetonides with aldehydes in a hydrocarbon solvent in the presence of perchloric acid and of high quantities (about 20 times by weight with respect to the organic substrate) of granular material (e.g., sand or ceramic material) in finely subdivided form.

In any case, the formation of acetals according to EP-A-262,108 is always conducted in organic solvent.

The methods for the preparation of budesonide and of its structural analogues above recalled are based on the acetalization of 16,17-diols or transketalization of having a free hydroxyl group at the 11β position.

EP-A-508,900 describes the preparation of budesonide by transketalization with butyraldehyde of of 11β-formyloxy or 9-halo-11β-formyloxy derivative of 21-acetoxy-16-α,17-α-dihydroxy-pregna-1,4-diene-3,20-dione, 16,17-acetonides in halogenated solvent, in the presence of perchloric acid, followed by alkaline solvolysis of the formyl group. The R epimer is prevalently obtained.

GB 1,469,575 describes the preparation of acetals or ketals of 16,17 dihydroxy pregnane derivatives by treatment with aldehydes or ketones of the corresponding 9β-11β-epoxides in aqueous hydrogen halides, in particular aqueous HF or HCl, to yield the corresponding 9-halo,11-hydroxy 16,17 acetals. This document does not provide any teaching regarding the epimeric control at the C-22 position of budesonide or of acetals structurally correlated thereto.

There is therefore felt the need to find new processes enabling a control of the ratio between the 22R and 22S epimers of budesonide and its structural analogues, so overcoming the drawbacks of the known methods.

SUMMARY

Now the applicant has surprisingly found that it is possible to control as desired the ratio between the 22R and 22S epimers of budesonide and its structural analogues by conducting the acetalization reaction in an aqueous hydrogen halide chosen from between HBr and HI, used as a reaction catalyst and solvent at the same time, thus obtaining high yields and high chemical purity of the acetals of formula (I) referred to hereinafter, in the desired 22R/22S epimeric ratio.

Altogether unexpectedly, the present process enables control of the aforesaid epimeric distribution independently of the type of substrate subjected to acetalization, and in particular irrespective of the presence of free or protected—OH groups in positions 11β- and/or 21, which, as previously seen, have considerable importance for the purposes of controlling the epimeric distribution according to prior art processes.

In particular, the acetalization or transketalization (also referred to as transacetalization) according to step a) of the present process altogether unexpectedly enables control of the ratio between the R epimers and the S epimers at the C-22 position on a vast range of substrates, regardless of their structure, even on pregnane derivatives having a double bond or an epoxide function between positions C-9 and C-11, which, to the knowledge of the applicant, have never been used as acetalization substrates in the preparation of budesonide and its analogues, and which are advantageously used because of their chemical stability and commercial availability at contained costs.

The present invention regards in particular a process for the preparation, with control of the epimeric distribution at the C-22 position, of acetals of formula (I)

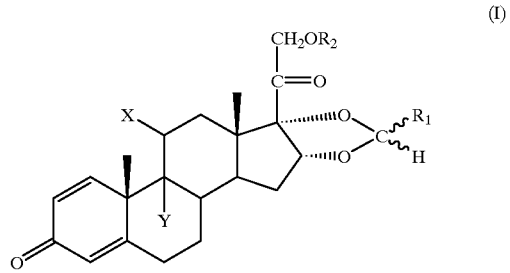

where $R_1$ is a linear or branched alkyl having from 1 to 12 carbon atoms;
$R_2$ is H, or a —CO—$Z_1$ acyl group, in which $Z_1$ is H or a linear or branched alkyl having from 1 to 12 carbon atoms;
X is β-OH; and
Y is H,
the said process comprising the following steps:
a) acetalization with control of the epimeric distribution at the C-22 position starting from a compound of formula (II)

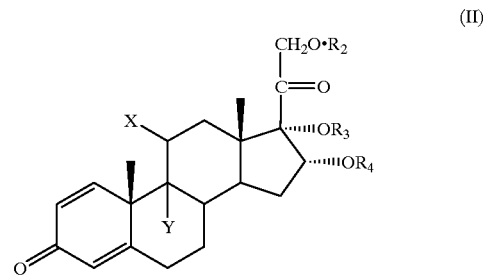

where $R_2$ has the meaning seen above;
$R_3$ and $R_4$ may both be H, or $R_3$ and $R_4$, taken together, may be:
  i) —C($R_5$)($R_6$)—, where $R_5$ and $R_6$, which may be the same or different from one another, are linear or branched alkyl groups having from 1 to 12 carbon atoms; or
$R_3$ and $R_4$, taken together, may be:
  ii) —CH($R_1$)—, where $R_1$ is an alkyl group as defined above;
X and Y may have one of the meanings A), B), C, or D), as specified below:
  A) X and Y, taken together, are an additional bond between C-9 and C-1;
  B) X is β-OH and Y is chosen from between H and an α-halogen;
  C) X is β-$OR_7$ and Y is chosen from between H and an α-halogen, where $R_7$ is a —CO—$Z_2$ acyl, in which $Z_2$ is H or a linear or branched alkyl having from 1 to 12 carbon atoms; or
  D) X and Y, taken together, are an —O— group;
    the said compound of formula (II) being treated with an aldehyde of formula $R_1$CHO, where $R_1$ has the meaning seen above, in the presence of a aqueous hydrogen halide chosen from between HBr and HI, and:
      when the compound of formula (II) is used where X and Y have the meaning A), B), or C), the corresponding acetals of formula (I) are obtained where X and Y are A), B), or C);

or, when the compound of formula (II) is used where X and Y have the meaning D), the corresponding acetals of formula (I) are obtained where X is β-OH and Y is an α-halogen, where the halogen is Br or I, depending on whether HBr of HI is used as hydrogen halide;

b) when in step a) the compound of formula (II) is used where X and Y have the meaning A), the corresponding acetals of formula (I) thus obtained (in which X and Y, taken together, represent an additional bond between C-9 and C-11) are treated with a halogenating agent in an acid environment in the presence of a hydroxylating agent, thus obtaining the corresponding acetals of formula (I) where Y is an α-halogen and X is β-OH, or with a halogenating agent in the presence of an acyloxylating agent, to yield the corresponding acetals of formula (I) where Y is an α-halogen and X is β-OR$_7$, defined as above;

c) when from step a) or step b) illustrated above the acetals of formula (I) are obtained in which X is β-OH or β-OR$_7$ and Y is a halogen as defined above, the acetals of formula (I) in which X is β-OH or β-OR$_7$ and Y is a halogen are treated with a dehalogenating agent, to yield the corresponding acetals of formula (I) in which Y is H;

d) when from steps a), b), or c) the acetals of formula (I) or formula (II) are obtained where R$_2$, R$_7$, or both, are acyl groups as defined previously, the other substituents being as defined previously, and the corresponding compounds of formula (I) or formula (II) in which R$_2$ and R$_7$ are H have to be obtained, the acyl group is removed, preferably by means of alkaline solvolysis.

Further objects of the present invention are the acetals of formula (I) in which R$_1$ is a linear or branched alkyl having from 1 to 12 carbon atoms, R$_2$ is H, or a —CO—Z$_1$ acyl group, in which Z$_1$ is H or a linear or branched alkyl having from 1 to 12 carbon atoms, and X and Y, taken together, are an additional bond between C-9 and C-11, as well as the process for their preparation, according to step a) seen previously.

DETAILED DESCRIPTION

In formula (I) the wavy lines between C-22 and the H and R$_1$ groups bonded to it indicate that these groups may be either above or below the plane of the sheet, and thus represent the existence of possible epimers at the C-22 position.

According to a particular embodiment of the present invention, the present process enables the compounds of formula (I) to be obtained as mixtures in 22R/22S ratios of between 60/40 and 50/50. According to another embodiment, it also enables mixtures to be obtained in which the R isomer further prevails (i.e., with 22R/22S ratios higher than 60/40).

The applicant has found that, in the conditions of acetalization or transketalization in aqueous HBr or HI according to the present invention, mixtures of 22R and 22S epimers where the S epimer prevails are generally formed in short periods of time, the S epimer then isomerizes to R epimer at a controlled rate. This enables the reaction mixture to be monitored and stopped when the desired epimeric ratio has been reached, thus obtaining at the same time complete conversion of the substrate and high yields of the desired 16,17-acetal, under temperature conditions suited to industrial processes.

The pattern of the reaction in aqueous HBr and HI is surprisingly different from the transketalization in aqueous HF, wherein at temperatures that enable complete conversion of the substrate into 16,17-acetal, the 22R epimer is prevalently obtained (22R/22S ratios $\geq$80/20), since it is not possible to isolate mixtures with the 22R/22S ratios equal to or lower than 60/40, given the high epimerization from S to R.

A further advantage of the use of aqueous HBr, which differentiates it, for example, from aqueous HCl, lies in its high solvent power, which enables the acetalization to be conducted in homogeneous phase, thus controlling in a more reliable way on an industrial scale the process of epimerization at the C-22 position.

The applicant has moreover unexpectedly found that the ratio between epimers at the C-22 position achieved in the acetalization phase in aqueous HBr or HI is substantially maintained in the subsequent steps b), c), or d), being in general increased by approximately 2–5 points in favour of the R epimer (presumably also following on isolation of the reaction intermediates by precipitation, for example, in an aqueous environment).

The process according to the present invention is particularly suited for obtaining budesonide [acetal of formula (I) in which R$_1$ is —(CH$_2$)$_2$CH$_3$, X is β-OH, Y is H, and R$_2$ is H].

The R$_1$, R$_5$, R$_6$ and Z$_2$ alkyl groups preferably have from 1 to 6 carbon atoms, and more preferably are CH$_3$.

When Z$_1$ and Z$_2$ are alkyl groups, they have preferably from 1 to 6 carbon atoms.

When R$_2$ and R$_7$ are acyl groups, they may in particular be formyl, acetyl, propionyl or butyryl. More preferably R$_2$ is a —COCH$_3$ group (Z$_1$=CH$_3$), and R$_7$ is an acetyl group (Z$_2$=CH$_3$), or a formyl group (Z$_2$=H).

When Y is halogen, it is preferably Cl, Br or I, more preferably Br.

According to typical embodiments of the present process, step a) is an acetalization conducted on the 16α,17α diols [compounds of formula (II), in which R$_3$=R$_4$=H], or a transketalization (also referred to as transacetalization) conducted on the 16,17-acetonides [compounds of formula (II) in which R$_3$ and R$_4$, taken together, are —C(CH$_3$)$_2$—].

Under the acetalization conditions according to the present process, it is also possible to convert the 22S epimers of the acetal of formula (I) into the corresponding 22R epimers. For example, subjecting a mixture of budesonide epimers in which the S epimer prevails to the acetalization conditions specified in step a), it is possible to prepare 22R/22S mixtures in ratios equal to or greater than 50/50 and to stop the conversion at the desired 22R/22S ratio.

According to a preferred embodiment of the present invention, step a) is carried out on the compounds of formula (II) having a double bond in position 9,11 [compounds of formula (II) in which X and Y, taken together, represent an additional bond between C-9 and C-11, R$_2$, R$_3$ and R$_4$ being defined as above], thus obtaining the corresponding acetals of formula (I), in which X and Y, taken together, represent an additional bond between C-9 and C-11, R$_1$ and R$_2$ being defined as above.

Subsequently, via step b), the halogen (preferably Cl or Br, more preferably Br) is introduced in position 9α, and the hydroxyl, or alternatively an acyloxyl (for example the formyloxy group), is typically introduced in position 11β, to yield respectively the acetal-halohydrin of formula (I), in which Y is an β-halogen and X is respectively β-OH or β-OR₇, where X is typically β-OH, and when X is β-OR₇, R₇ is preferably formyloxy (—OCO—H).

According to another embodiment of the present invention, in step a) the compounds of formula (II) are used as substrates, where X is β-OH or β-OR₇ and Y is an α-halogen, where the halogen is preferably Br, R₂, R₃ and R₄ being as defined above, to yield the corresponding acetals of formula (I) in which X is β-OH or β-OR₇, where R₇ is as defined above, and Y is an α-halogen, preferably Br, R₁ and R₂ being as specified above.

9β,11β-epoxides may moreover be used [these being compounds of formula (II) in which X and Y, taken together, are —O—, R₂, R₃ and R₄ having the meaning referred to above], which under the present acetalization or transketalization conditions yield the corresponding 9,11 halohydrins [acetals for formula (I) in which X is β-OH and Y is an α-halogen, where R₁ and R₂ have the meaning seen above and the halogen is Br or I depending on whether step a) is carried out in HBr or HI, respectively].

The acetals of formula (I) halogenated in position 9α obtained from the halohydrins or epoxides of formula (II) referred to above, through step a) or step b) as previously described, are then subjected to dehalogenation according to step c), to yield the corresponding acetals of formula (I) in which Y is H (where R₁, R₂ and R₇ are as defined above, and X is β-H or β-OR₇).

According to another embodiment of the present invention, in step a) is carried out on the compounds of formula (II) in which X is β-OH or β-OR₇ and Y is H, the other substituents being defined as above, thus directly obtaining the acetals of formula (I) in which X β-OH or β-OR₇ and Y is H, R₁ and R₂ being as defined above.

When ester functions are present and the acetals of formula (I) in which R₂ and R₇ are H, have to be obtained, an alkaline solvolysis according to step d) is performed, which may be carried out in any phase of the process but is preferably carried out as the last step, on the acetals of formula (I) in which R₂, R₇ or both are acyl as defined previously and Y is H, which come from the dehalogenation step c).

According to a further preferred embodiment of the present invention, the present process is carried out starting from the compounds of formula (II) in which X and Y, taken together, are an additional bond between C-9 and C-11, represented by the formula (II-A)

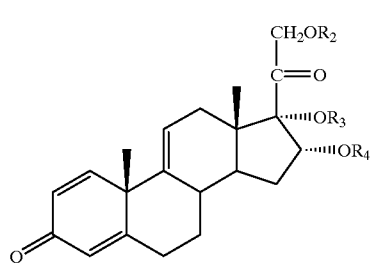

(II-A)

in which R₂ is as defined above, preferably in the form of 16,17-diols [R₃=R₄=H] or of 16,17-acetonides [R₃ and R₄, taken together, are a —C(CH₃)₂- group].

The compounds of formula (II-A) in which R₃ and R₄ are H are known from patents U.S. Pat. No. 2,998,443 and U.S. Pat. No. 3,047,468, or may be prepared with the methods therein described. The corresponding acetonides may be prepared from the 16,17 diols using conventional techniques, for example by treatment with acetone in an acid environment. A number of compounds of formula (II-A), among which those in which R₂ is H or acetyl, as well as the corresponding 16,17-acetonides, are available on the market, and are sold by UPJOHN.

The compounds of formula (II-A) are then converted into the acetals of formula (I) in which X is β-OH and Y is H, preferably carrying out steps a), b), c) and d) sequentially.

From the acetalization of the compounds of formula (II-A) the corresponding acetals of formula (I-A) are obtained

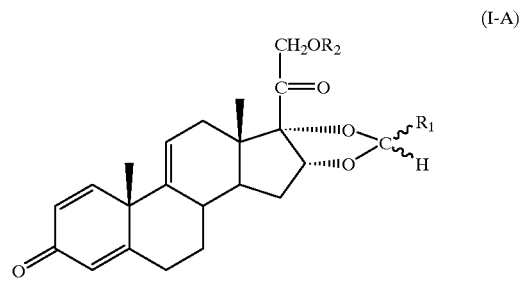

(I-A)

in which R₁ and R₂ have the meaning seen previously; these acetals are then subjected to step b), which is preferably a halohydroxylation, preferably conducted via treatment with a chlorinating or brominating agent, more preferably a brominating agent, in the presence of a hydroxylating agent, such as water, to yield the halohydrins (I-B)

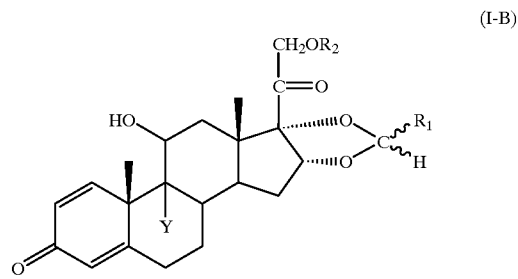

(I-B)

in which R₁ and R₂ have the meaning seen above, and Y is an β-halogen, preferably Cl or Br, more preferably Br.

The acetals-halohydrins of formula (I-B) are then subjected to dehalogenation, according to the method specified in step c), to yield the acetal of formula (I-1)

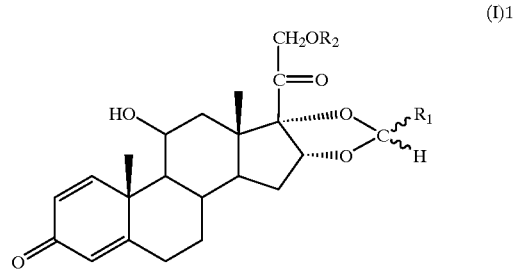

(I)1 in which R₁ and R₂ have the meaning seen above.

When R₂ is an acyl group, and the acetals of formula (I-1) in which R₂ is H have to be obtained, an alkaline solvolysis step is typically carried out, which is preferably performed as the final step of synthesis, on the acetal of formula (I-1) in which R₂ is an acyl coming from step c).

According to another typical embodiment of the present invention, the compounds of formula (II), in which X is β-OH and Y is an α-halogen represented by the formula (II-B1) are used as acetalization substrates.

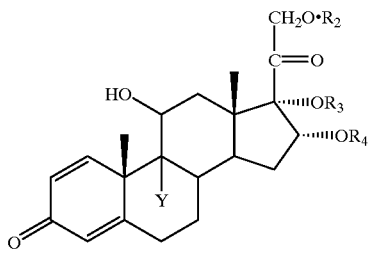

(II-B1)

in which $R_2$ is as defined above, and Y is a halogen, for example Cl or Br, preferably Br, preferably used as 16,17-diols [$R_3=R_4=H$] or as 16,17-acetonides [$R_3$ and $R_4$, taken together, are —C(CH$_3$)$_2$—].

Various compounds of formula (II-B1) are known compounds, or may in any case be prepared using conventional methods. In particular, the halohydrins of formula (II-B1) in which Y is α-Br are commercially available.

When subjected to step a), the halohydrins of formula (II-B1) yield the corresponding acetals of formula (I-B) referred to previously, in which $R_1$ and $R_2$ have the meaning seen above, and Y is Cl or Br, preferably Br, which are then subjected to the dehalogenation step c) to yield the acetals of formula (I-1) previously defined, which, if so required, are subjected to alkaline solvolysis step according to d) to convert the acetals of formula (I-1) in which $R_2$ is an acyl as defined above into the corresponding acetals of formula (I-1) in which $R_2$ is H.

According to a further embodiment of the present invention, the acetalization step a) is carried out on the compound of formula (II) in which X is β-OH and Y is H, indicated below with the formula (II-B2)

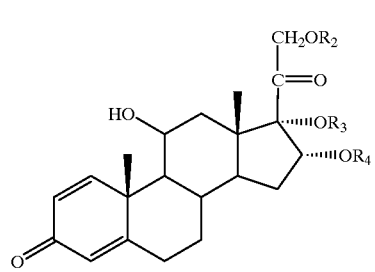

(II)B2 in which $R_2$ is H or —COZ$_1$ acyl, where Z$_1$ is as defined previously, preferably in the form of 16,17-diols [$R_3=R_4=H$] or of 16,17-acetonides [$R_3$ and $R_4$, taken together are a —C(CH$_3$)$_2$— group].

Also in this case, the synthesis may be completed with alkaline solvolysis when $R_2$ is an acyl, preferably performed as the final step on the acetals of formula (I) in which Y is H.

According to another embodiment of the present invention, the acetalization step a) is carried out on the 9β,11β-epoxides of formula (II) in which X and Y, taken together, are —O—, represented by the formula (II-D)

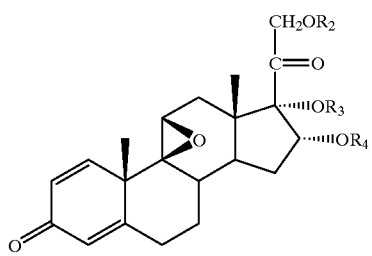

(II)-D in which $R_1$ and $R_2$ are as defined previously, preferably in the form of 16,17-diols [$R_3=R_4=H$] or of 16,17-acetonides [$R_3$ and $R_4$, taken together, are a —C(CH$_3$)$_2$— group].

Various 9,11 epoxides of formula (I) are known compounds, or in any case are obtained using conventional techniques. In particular, the epoxides of formula (II-D) in which $R_2$ is H or an acetyl, $R_3=R_4=H$, or $R_3$ and $R_4$, taken together are —C(CH$_3$)$_2$—, are products available on the market.

After acetalization of the compounds of formula (II-D) according to step a) the corresponding halohydrins of formula (I-B) referred to previously are obtained, in which $R_1$ and $R_2$ have the meaning seen previously, and Y is Br or I according to the hydrogen halide used in step a). These halohydrins are then subjected to dehalogenation according to step c), to yield the corresponding acetals of formula (I-1) referred to above. If so required, an alkaline solvolysis step is performed, preferably as the final step of synthesis, to convert the acetals of formula (I-1) coming from step c), in which $R_2$ is an acyl, into the corresponding acetals (I-1) in which $R_2$ is H.

According to a typical embodiment of the present invention, step a) is carried out reacting substrates of formula (II) (e.g., 16α,17α diols or acetonides) with the aldehyde of formula R$_1$CHO, preferably in molar ratios of between 1:1 and 1:5, more preferably of between 1:3 and 1:4, expressed as moles of aldehyde to moles of the substrate of formula (II).

The aqueous halogen halide has a concentration of between approximately 20% and approximately 70% w/w (weight/weight) of acid in water. Preferably aqueous HBr is used having a concentration of approximately 48–62%, typically of approximately 48%, or aqueous HI having a concentration of approximately 56–67%, typically of approximately 55–57%, corresponding to commercially available products (w/w percent of acid in water).

Preferably, step a) is performed at temperatures of between approximately −10° C. and +30° C., more preferably of between approximately −2° C. and +2° C.

Preferably, step a) is carried out using from 1 to 20 parts by volume, more preferably approximately 10 parts by volume, of aqueous HBr or HI per part by weight of compound of formula (II); furthermore, the quantity of water present in the acetalization environment typically ranges from 1 to 10 parts by volume per part by weight of substrate, preferably from 5 to 8.

In the present text, the parts by volume per part by weight are expressed as millilitres per gram or corresponding multiples.

According to typical conditions of implementation of the present invention, step a) is carried out in an aqueous hydrogen halide alone as reaction solvent. Possibly, a co-solvent that can be mixed with water (e.g., tetrahydrofuran) may be added, generally in the minimum quantity required for solubilizing the substrate and obtaining a reaction mixture in homogeneous phase. For this purpose, the co-solvent is added in a minority amount with respect to the aqueous hydrogen halide, for example less than or equal to 20% by volume with respect to the aqueous acid.

Generally, from step a) the acetals of formula (I) are obtained with a 22R/22S epimer ratio of between approximately 60/40 and 50/50, operating with reaction times of approximately 0.5–6 hours, for example of from 2 to 6 hours, and mixtures of epimers with 22R/22S ratios higher than 60/40, typically of between 60/40 and 90/10, operating with reaction times generally of over 10 hours.

Upon complete conversion of the substrate of formula (II) into acetal, it is possible to slow down considerably the process of formation of the R epimer by diluting the reaction mixture with water, for example with approximately from 1 to 6 parts by volume of water per part by weight of substrate.

The acetals of formula (I) are typically isolated from the reaction mixture by precipitation, diluting the reaction mixture approximately 1:10 v/v (volume/volume) with water, at cool temperature (approximately 0−/+5° C.).

Step b) is, for example, carried out at a temperature of between −10° C. and +20° C. The halogenating agent of the present step b) is preferably a chlorinating or brominating agent, more preferably a brominating agent, for example an N-chloro- or N-bromo-amide, phthalimide or succinimide, or an N,N-dichloro- or N,N-dibromo-dimethyl hydantoin, typically an N,N-dibromodimethyl hydantoin.

Step b) is preferably carried out in an acid environment, typically in the presence of a strong acid, such as perchloric acid or fluoboric acid.

Step b) of the invention may be conveniently carried out in the presence of a co-solvent, such as dioxane or dimethylsulphoxide.

Preferably, step b) is a halo-hydroxylation step, performed using a halogenating agent in the presence of a hydroxylating agent, typically water, to yield the halohydrins-acetals of formula (I) in which X is β-OH and Y is an α-halogen.

For example, the halo-hydroxylation according to step b) of the invention may be performed with a halogenating and hydroxylating agent, such as HClO or HBrO, or with precursors thereof, for example $Br_2$ or $Cl_2$ in the presence of water.

In typical conditions, the halo-hydroxylation step b) of the present invention is carried out with dibromodimethyl hydantoin and water, in the presence of a strong acid, more typically using dibromodimethyl hydantoin, in the presence of perchloric acid, in dioxane/water, at a temperature typically of between −10° C. and +20° C.

Alternatively, halo-acyloxylation may be performed treating the acetal of formula (I) in which X and Y, taken together, are an additional bond between C-9 and C-11, with a halogenating agent, in the presence of an acyloxylation agent, in particular a formyloxylation agent, in an anhydrous and acid environment, to obtain the compounds of formula (I) in which X is β-$OR_7$, where $R_7$ is an acyl as defined above. In particular, it is possible to introduce in position 11, the formyloxy group [X =β-$OR_7$ where $R_7$ is -H], carrying out step b) with a halogenating agent, for example an N-halogen-amide, succinimide or dimethyl hydantoin, in an anhydrous environment, in the presence of a formyloxylating agent, such as dimethyl formamide, or formic acid. For example, dibromodimethyl hydantoin in dimethyl formamide, in the presence of perchloric acid, at a temperature of between −10° C. and +20° C., can be used.

The intermediates obtained from step b) are typically isolated by adding water to the reaction mixture.

Step c) is typically carried out at approximately +50/+70° C.

The dehalogenating agent is typically an organotin hydride, such as tributyltin hydride, used typically in the presence of a radical reaction initiator, such as azobisisobutyronitrile or benzoyl peroxide, generally operating an ether solvent (e.g., isopropyl ether, ethyl ether, tetrahydrofuran), in ethyl acetate, in acetonitrile, in an aromatic solvent (e.g., toluene), or in an aprotic polar solvent, such as dimethyl formamide.

According to a typical embodiment of the present invention, tributyltin hydride is used, in the presence of azobisisobutyronitrile, for example operating in isopropyl ether, preferably at a temperature of between +48° C. and +69° C.

The dehalogenation may also be performed for instance with tin (0) or lead (0), or with a salt of tin (II) or lead (II), in the presence of a hydrogen donor (such as thiol for example ethane thiol 1,3-propane-dithiol, butane thiol, mercaptoacetic acid, 3-mercaptopropionic acid, hydrophosphorous acid), and of one of the aforementioned radical initiators, in the presence of the solvents referred to previously. It is also possible to use derivatives of chromium (II), such as carboxylates (e.g. acetates or stearates), in the presence of one of the above-mentioned hydrogen donors and in polar solvents, such as dimethyl formamide, dimethylsulphoxide, dimethylacetamide, or to use tris-(trimethylsilyl) silane in the presence of one of the aforementioned radical reaction initiators.

The alkaline solvolysis is preferably an alcoholysis carried out by treatment with an alkaline hydroxide, such as sodium hydroxide or potassium hydroxide, in a catalytic quantity, in an alcoholic solvent, such as methanol or ethanol, possibly in the presence of an organic co-solvent, such as methylene chloride, chloroform, dioxane, tetrahydrofuran, and ethyl acetate, preferably methylene chloride, at temperatures of typically between −10° C. and +10° C. Alternatively, the alkaline solvolysis may also be an alkaline hydrolysis, carried out by treatment with alkaline or alkaline-earth hydroxides, at least in a stoichiometric amount, in an aqueous environment, in the presence of co-solvents such as the ones referred to for alcoholysis, for example at temperature of between −10° C. and +10° C.

Given below are a few examples, which have the aim of illustrating the present invention, without, however, limiting in any way the scope thereof.

COMPARATIVE TEST 1

Acetalization with butyraldehyde in dioxane/$HClO_4$ of compound of formula (II) in which $R_2$=H, $R_3$=$R_4$=H, X and Y, taken together, are an additional bond between C-9 and C-11 (substrate 1)

20 grams of substrate 1 are added, under stirring, to a mixture consisting of 200 ml of dioxane and 10 ml of butyraldehyde. At room temperature (approximately between +20 and +25° C.) and under nitrogen, 2 ml of 70% perchloric acid in anhydrous acetic acid are added. After reacting for 3 hours at the above temperature, the reaction mass is poured into 2000 ml of water, previously cooled down to approximately 5° C. A suspension is obtained, which is vacuum-filtered. The isolated solid is washed with water until a neutral pH is obtained. The product is vacuum-dried at room temperature until constant weight is achieved to obtain 20 grams of derivative of formula (I) in which X and Y, taken together, are an additional bond between C-9 and C-11, and $R_1$ is —$(CH_2)_2CH_3$ and $R_2$ is H, having a 22R/22S ratio of 40/60.

COMPARATIVE TEST 2

Acetalization with butyraldehyde in dioxane/$HClO_4$ compound of formula (II) in which X is β-OH, Y is α-Br, $R_3$=$R_4$=H, and $R_2$ is —$COCH_3$ (substrate 2)

20 grams of substrate 2 are treated as described in Comparative Test 1 to obtain 20 grams of product of formula (II) in which X is β-OH, Y is α-Br, $R_1$ is —$(CH_2)_2CH_3$, and $R_2$ is —$COCH_3$, having a 22R/22S ratio of 34/66.

COMPARATIVE TEST 3

Acetalization with butyraldehyde in dioxane/$HClO_4$ following 16α,17α diols of formula (II) in which $R_3$=$R_4$=H, and in which:

X and Y, taken together, are —O—, $R_2$ is H (substrate 3);
X is β-OH; Y is α-Br; $R_2$ is H (substrate 4);
X is β-OH; Y is H; $R_2$ is H (substrate 5)

are treated as described in comparative test 1.

Table 1 gives the 22R/22S ratios of the acetals of formula (I) obtained from the Comparative Tests 1–3:

TABLE 1

| Substrate | Position 9, 11 | Position 21 | Acetal 22R:22S |
|---|---|---|---|
| 1 | delta 9, 11 | $R_2$ = H | 40:60 |
| 2 | 11 β-OH; 9 α-Br | $R_2$ = $COCH_3$ | 34:66 |
| 3 | 9, 11 epoxide | $R_2$ = H | 16.5:73.5 |
| 4 | 11 β-OH; 9 α-Br | $R_2$ = H | 56.5:43.5 |
| 5 | 11 β-OH; Y = H | $R_2$ = H | 50:50 |

EXAMPLE 1

Preparation of budesonide from the compound of formula (II) in which $R_2$ is H, $R_3$=$R_4$=H, and X and Y, taken together, are an additional bond between C-9 and C-11 (substrate 1)

a) Acetalization –20 grams of substrate 1 are added to a mixture consisting of 200 ml of 48% aqueous hydrobromic acid in 20 ml of butyraldehyde, pre-cooled down to 0° C. and kept stirred. Immediately after the addition of substrate 1, a sample is taken from the reaction mass, determining via HPLC the ratio between the epimers at the C-22 position, which proves to be R/S=30/70. The reaction mass is allowed to react at approximately 2° C. for 45 minutes, the reaction mass is poured into 2000 ml of water pre-cooled to 5° C., the suspension obtained is vacuum-filtered, and the solid thus isolated is washed with water until neutral pH is reached. The solid is vacuum-dried down to constant weight to obtain 20 grams of the compound 6 [derivative of formula (I) in which X and Y, taken together, are an additional bond between C-9 and C-11, $R_1$ is —$(CH_2)_2CH_3$, and $R_2$ is H] having an R/S ratio of 51/49.

b) Hydroxybromination—The intermediate 6 obtained from the previous step is treated with dibromodimethyl hydantoin, in dioxane/water, in the presence of 70% perchloric acid at a temperature of 15° C. After 30 minutes, the reaction mixture is buffered with sodium sulphite and poured into 1000 ml of $H_2O$. Approximately 23 grams of the intermediate 7 [derivative of formula (I) in which $R_1$ is$(CH_2)_2CH_3$, $R_2$ is H, X is β-OH, and Y is α-Br] are obtained.

c) Debromination—The intermediate 7 obtained from the previous step is treated with tributyltin hydride in isopropyl ether, in the presence of azobisisobutyronitrile (AIBN), at 60° C. After 5 hours, the reaction mixture is vacuum-concentrated to a small volume. Budesonide is obtained as a 22R/22S epimer mixture of 53/47.

EXAMPLE 2

Preparation of budesonide starting from the compound of formula (II) in which X and Y, taken together, are —O—, $R_3$=$R_4$=H, and $R_2$ is H (substrate 3)

a) Acetalization—Acetalization is carried out as described in Example 1, step a), starting from 20 g of substrate 3. A sample is taken, and it is found that the HPLC ratio between the epimers at the C-22 position is 37/68. The reaction is carried on at 0° C. for approximately 60 minutes and worked up as described in Example 1, step a), to obtain, after drying to constant weight, 24 grams of bromhydrin 7 [derivative of formula (I) in which $R_1$ is —$(CH_2)_2CH_3$, $R_2$ is H, X is β-OH, and Y is α-Br], with a 22R/22S ratio of 50.5/49.5.

c) Debromination—The intermediate 7 is treated as described in step c) of Example 1 to obtain budesonide as an R/S epimer mixture of 52.5/47.5.

EXAMPLE 3

Preparation of budesonide from the compound of formula (II) in which X is α-OH, Y is α-Br, $R_2$ is —$COCH_3$, and $R_3$=$R_4$=H (substrate 2)

a) Acetalization is performed as described in Example 1, step a), starting from 20 grams of substrate 2, adding 40 ml of tetrahydrofuran to the aqueous HBr and the butyraldehyde. At the end of the addition of substrate 2, the HPLC ratio between the R/S epimers at the C-22 position is R/S =50/50 (after approximately 120 minutes at approximately 2° C.). Work-up is carried out as described in Example 1, and after drying the product thus obtained to constant weight, 20.5 grams of the intermediate 8 are obtained [product of formula (I) in which X is β-OH, Y is α-Br, $R_1$ is —$(CH_2)_2CH_3$, and $R_2$ is —$COCH_3$], with a 22R/22S ratio of 49.5/50.5.

c) Debromination—Debromination of the intermediate 8 is carried out as described in step c) of Example 1, to obtain the intermediate 9 [product of formula (II) in which X is β-OH, Y is H, $R_1$ is —$(CH_2)_2CH_3$, and $R_2$ is —$COCH_3$].

d) Alkaline solvolysis—The intermediate 9 is treated with 30% aqueous sodium hydrate, in methanol/methylene chloride, at a temperature of approximately 5° C., to isolate, after 2 hours, budesonide as a mixture of 22R and 22S epimers with a ratio R/S=55/45.

EXAMPLE 4

Preparation of budesonide from the derivative of formula (II) in which X is β-OH, Y is α-Br, $R_2$ is —$COCH_3$, and $R_3$ and $R_4$, taken together, are —$C(CH_3)_2$— (substrate 10)

a) Acetalization is performed as described in Example 1, step a), starting from 20 grams of substrate 10, replacing HBr with an equal volume of 55–57% aqueous HI. After approximately 150 minutes at approximately +2° C., upon complete transketalization (starting material less than 0.25%), the reaction mixture is worked as described in Example 1, step a), adding to the 2000 ml of water 5 grams of sodium metabisulphite. The suspension thus obtained is filtered, the solid obtained is washed with water until a neutral pH is reached, and vacuum-dried to constant weight to obtain 20 grams of the intermediate 7, with a 22R/22S ratio of 51/49.

c) Debromination of the intermediate 7 is carried out as described in step c) of Example 1. Then alkaline solvolysis is performed, as described in the subsequent example, to obtain budesonide as an R/S epimer mixture with the following ratio: 53.5/46.5.

EXAMPLE 5

Preparation of budesonide from desonide-21-acetate [derivative of formula (I) in which X is β-OH, Y is H, $R_2$ is —$COCH_3$, and $R_3$ and $R_4$, taken together, are —$C(CH_3)_2$— (substrate 11)]

a) Acetalization is performed as described in Example 4, step a), starting from 20 grams of substrate 11. After approximately 180 minutes at approximately 2° C. (substrate 11 less than 0.25%), the reaction mass is poured into 2000 ml of water pre-cooled to 5° C. and containing 5 grams of sodium metabisulphite. The suspension thus obtained is filtered, and the solid obtained is washed with water until a neutral pH is reached. The damp solid is used in the subsequent phase.

a) Alkaline solvolysis—The intermediate 12 obtained from the previous step is treated with sodium hydrate in methanol/methylene chloride, as described in Example 3, step d), to obtain budesonide as an R/S epimer mixture with the following ratio: 53.6/46.4.

What is claimed is:

1. Process for the preparation, with control of the epimeric distribution at the C-22 position, of acetals of formula (I)

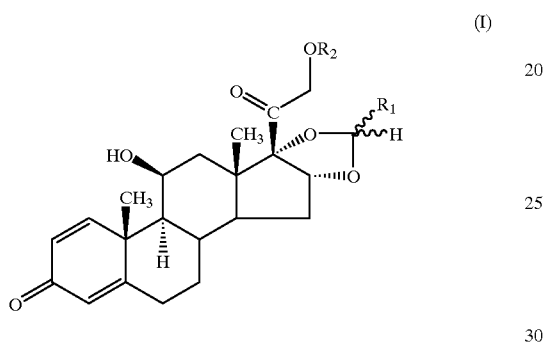

(I)

where $R_1$ is a linear or branched alkyl having from 1 to 12 carbon atoms; $R_2$ is H, or a —CO—$Z_1$ acyl group, in which $Z_1$ is H or a linear or branched alkyl having from 1 to 12 carbon atoms, the said process comprising the following steps:

a) acetalization with control of the epimeric distribution at the C-22 position, starting from a compound of formula (II-A)

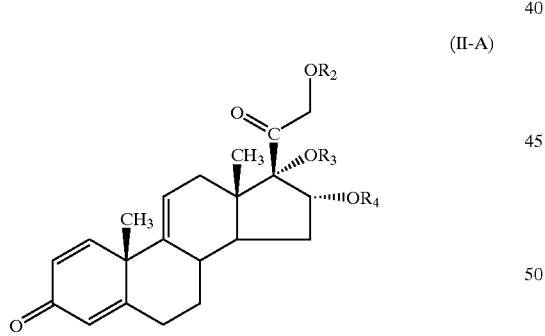

(II-A)

where $R_2$ has the meaning seen above; $R_3$ and $R_4$ may both be H, or $R_3$ and $R_4$, taken together, may be:
(i) —C($R_5$)($R_6$)—, where $R_5$ and $R_6$, which are the same or different from one another, are linear or branched alkyl groups having from 1 to 12 carbon atoms; or
(ii) —CH($R_1$)—, where $R_1$ is an alkyl group as defined above; in which the said compound of formula (II-A) is treated with an aldehyde of formula $R_1$CHO, where $R_1$ has the meaning seen above, in the presence of an aqueous hydrogen halide chosen from between HBr and HI, and the corresponding acetals of formula (I-A) are obtained

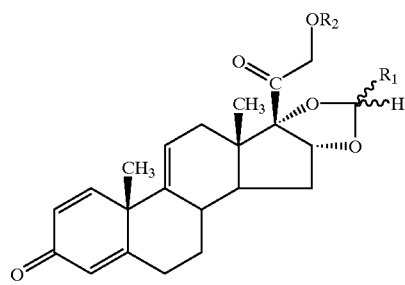

(I-A)

wherein $R_1$ and $R_2$ have the above meaning;

b) the acetals of formula (I-A) thus obtained are treated with a halogenating agent in an acid environment in the presence of a hydroxylating agent or in the presence of an acyloxylating agent, thus obtaining the corresponding acetals of formula (I-C)

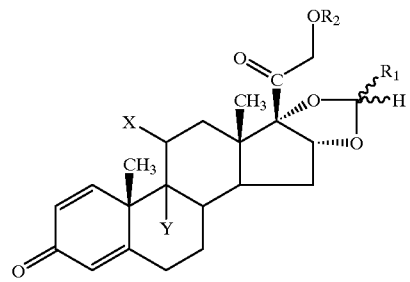

(I-C)

where Y is an α-halogen and X is β-OH when the reaction is carried out in the presence of a hydroxylating agent, or X is β-O$R_7$, where $R_7$ is a CO—$Z_2$ acyl in which $Z_2$ is H or a linear or branched alkyl having from 1 to 12 carbon atoms, when the reaction is carried out in the presence of an acyloxylating agent;

c) the so obtained acetals of formula (I-C) in which Y is α-halogen, are treated with a dehalogenating agent to yield the corresponding acetals of formula (I) reported above when X is β-OH, and to yield the acetals of formula (I-D)

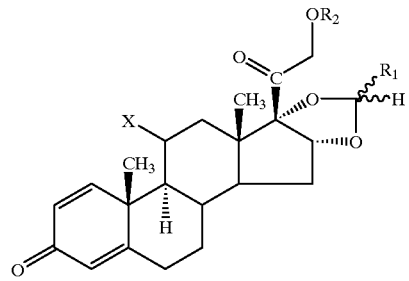

(I-D)

in which $R_1$, $R_2$ have the above meaning, and X is β-O $R_7$, where $R_7$ is as defined above;

d) the acetals of formula (I-A), (I-C), (I-D), or formula (I) coming from step a), b) or c) where $R_2$, $R_7$ or both, are acyl groups as defined previously, and the other substituents are as defined previously, are subjected to removal of the ester group, when the corresponding acetals of formula (I-A), (I-C), (I-D), or formula (I) in which $R_2$ and $R_7$ are H have to be obtained.

2. Process according to claim 1, in which:
in step b) the acetals of formula (I-A) coming from step a) are subjected to halohydroxylation to yield the halohydrins (I-B)

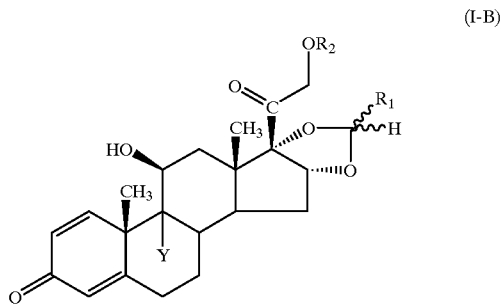

(I-B)

in which $R_1$ and $R_2$ are as defined in claim 1, and Y is an α-halogen;
step c) is carried out, in which the acetals-halohydrins of formula (I-B) are subjected to dehalogenation to yield the acetals of formula (I-1)

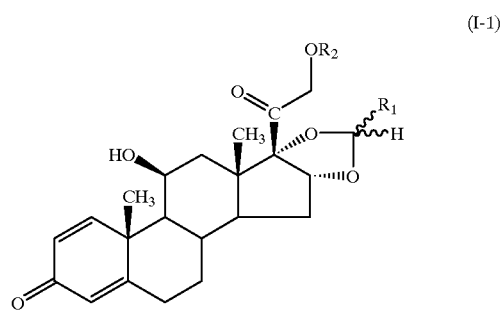

(I-1)

in which $R_1$ and $R_2$ are as defined in claim 1;
in step d) when $R_2$ is an acyl group and the acetals of formula (I-1) in which $R_2$ is H have to be obtained, the acyl group is removed by alkaline solvolysis.

3. Process according to claim 1, in which the acetals of formula (I) are obtained as 22R/22S mixtures having ratios of between 60/40 and 50/50.

4. Process according to claim 1, for the preparation of budesonide.

5. Process according to claim 1, in which the alkyl groups $R_1$, $R_5$, $R_6$ or $Z_2$ have from 1 to 6 carbon atoms; when $Z_1$ and $Z_2$ are alkyl groups, have from 1 to 6 carbon atoms; when $R_2$ and $R_7$ are acyl groups, they are chosen from among formyl, acetyl, propionyl or butyryl; when Y is a halogen, it is chosen from among Cl, Br and I.

6. Process according to claim 5, in which the $R_1$, $R_5$, $R_6$ or $Z_2$ groups are $CH_3$ groups; when $R_2$ and $R_7$ are acyl groups, $R_2$ is a —$COCH_3$ group ($Z_1$=$CH_3$), and $R_7$ is an acetyl group ($Z_2$=$CH_3$), or a formyl group ($Z_2$=H); when Y is a halogen, it is Br.

7. Process according to claim 2, in which Y is Cl or Br.

8. Process according to claim 2, in which Y is Br.

9. Process according to claim 1, in which step a) is carried out on the compound of formula in which $R_3$=$R_4$=H, or $R_3$ and $R_4$, taken together, are —$C(CH_3)$—.

10. Epimerization process comprising converting the 22-S epimer of an acetal of formula (I) as defined in claim 1 into the corresponding 22-R epimer, by subjecting it to the conditions indicated in step a) as defined in claim 1.

11. Process according to claim 1, in which the molar ratios between the aldehyde of formula $R_1CHO$ and the substrate of formula (II) are of between 1:1 and 1:5.

12. Process according to claim 11, in which the molar ratios between the aldehyde of formula $R_1CHO$ and the substrate of formula (II-A) are of between 1:3 and 1:4.

13. Process according to claim 1, in which in step a) aqueous hydrogen halide is used having a concentration of between 20% and 70% weight by weight of acid in water.

14. Process according to claim 13, in which aqueous HBr is used with a concentration of approximately 48%, or aqueous HI with a concentration of approximately 55–57%.

15. Process according to claim 1, in which step a) is performed using from 1 to 20 parts by volume of aqueous HBr or HI per part by weight of compound of formula (II-A).

16. Process according to claim 15, in which 10 parts by volume of aqueous HBr or HI are used per part by weight of compound of formula (II-A).

17. Process according to claim 1, in which step a) is carried out at temperatures of between −10° C. and +30° C.

18. Process according to claim 17, in which step a) is carried out at temperatures of between approximately −2° C. and +2° C.

19. Process according to claim 1, in which step a) is carried out for reaction times of between 0.5 and 6 hours, to obtain 22R/22S epimer ratios of between 60/40 and 50/50.

20. Process according to claim 1, in which step a) is carried out with reaction times of over 10 hours, to obtain 22R/22S epimer ratios of between 60/40 and 90/10.

21. Process according to claim 1, in which step a) is carried out in the presence of a co-solvent that can be mixed with water in amount less than or equal to 20% by volume with respect to the aqueous hydrogen halide.

22. Process according to claim 1, in which step b) is carried out at a temperature of between −10° C. and +20° C.

23. Process according to claim 1, in which step b) is a halohydroxylation step conducted by treatment with a chlorinating or brominating agent, in the presence of a hydroxylating agent.

24. Process according to claim 23, in which a brominating agent is used.

25. Process according to claim 23, in which the halogenating agent is selected from the group consisting of:
i) N-chloro- or N-bromo-amide, phthalimide or succinimide,
ii) N,N-dichloro- or N,N-dibromo-dimethyl hydantoin,
iii) HClO,
iv) HBrO, and
v) $Br_2$ or $Cl_2$ in the presence of water.

26. Process according to claim 23, in which step b) is carried out using dibromodimethyl hydantoin, in the presence of a strong acid and water.

27. Process according to claim 1 or claim 7, in which step b) is carried out using a halogenating agent selected from the group consisting of N-halogen amides, N-halogen succinimides and N-halogen dimethyl hydantoins, in an anhydrous environment, in the presence of a formyloxylating agent chosen from between dimethyl formamide and formic acid.

28. Process according to claim 1, in which the dehalogenation step c) is carried out at +50° C.–+70° C.

29. Process according to claim 1, in which step c) is carried out using an organotin hydride, in the presence of a radical reaction initiator.

30. Process according to claim 29, in which tributyltin hydride is used, in the presence of azobisisobutyronitrile.

31. Process according to claim 1, in which step d) is an alcoholysis step carried out by treatment with an alkaline hydroxide, in a catalytic quantity, in an alcoholic solvent, optionally in the presence of an organic co-solvent, at temperatures of between −10° C. and +10° C.

* * * * *